United States Patent [19]
Wade et al.

[11] Patent Number: 5,167,398
[45] Date of Patent: Dec. 1, 1992

[54] QUICK DISCONNECT COUPLER

[75] Inventors: Richard B. Wade, Laguna Beach; David Chu, La Palma, both of Calif.

[73] Assignee: Bridge Products, Inc., Northbrook, Ill.

[21] Appl. No.: 652,853

[22] Filed: Feb. 8, 1991

[51] Int. Cl.$^5$ ............................................. F16L 37/28
[52] U.S. Cl. ................................ 251/149.6; 251/361
[58] Field of Search ............................ 251/361, 149.6

[56] References Cited

U.S. PATENT DOCUMENTS

| | | | |
|---|---|---|---|
| 2,265,267 | 12/1941 | Cowles | 251/149.6 |
| 2,433,119 | 12/1947 | Hansen | 285/169 |
| 2,653,792 | 9/1953 | Sacchini | 251/122 |
| 2,673,062 | 3/1954 | Cornelius | 251/144 |
| 2,905,485 | 9/1959 | Zajac | 284/18 |
| 3,567,175 | 3/1971 | Sciuto, Jr. | 251/149.6 |
| 3,583,667 | 6/1971 | Amneus | 251/149.6 |
| 4,366,945 | 1/1983 | Blävenstein | 251/149.6 |
| 4,825,893 | 5/1989 | Gailey | 251/149.6 |
| 4,833,951 | 5/1989 | Karcher et al. | 29/213.1 |

FOREIGN PATENT DOCUMENTS

| | | |
|---|---|---|
| 635238 | 1/1962 | Canada . |
| 607340 | 1/1948 | United Kingdom . |
| 2069083 | 8/1981 | United Kingdom ............ 251/149.6 |

OTHER PUBLICATIONS

Brochure, Tuthill Corporation, Hansen Coupling Division, Cleveland, Ohio, date unknown.
"Hansen ATUO-FLO 20", Hansen Coupling Division, Cleveland, Ohio, date unknown.
Amflo Catalog p. 4, Santa Ana, Calif., "Couplers and Plugs", date unknown.

*Primary Examiner*—A. Michael Chambers
*Attorney, Agent, or Firm*—Willian Brinks Olds Hofer Gilson & Lione

[57] ABSTRACT

A quick disconnect coupler includes a seal retaining member movably in a coupler housing. A sealing washer biases the retaining member toward first position, and an annular seal is mounted in the retaining member. This annular seal defines both axial and radial sealing surfaces, and it is configured to transmit sufficient force to the seal retaining member to move the seal retaining member to a rearward position in response to a first, larger diameter plug bearing on the axial sealing surface, and to form a radial seal around a second, smaller diameter plug.

16 Claims, 3 Drawing Sheets

QUICK DISCONNECT COUPLER

BACKGROUND OF THE INVENTION

This invention relates to a quick disconnect coupler having a seal which can be shaped to seal against all three of the commonly used coupler plugs.

Quick disconnect couplers are in widespread use for releasably joining pneumatic and fluid transfer lines. In general, quick disconnect couplers use hardened balls or pins which engage a groove in the coupler plug to hold it securely against a soft seal while permitting the assembly to swivel, thereby preventing kinking or twisting of hoses. A sliding sleeve is manually retracted to release the locking balls or pins, thereby permitting the plug to be inserted or removed. The sleeve automatically returns to the lock position when released. Generally, an automatic shut-off valve is provided in the coupler to seal the central passageway of the coupler automatically upon uncoupling. This eliminates the need for a separate shut-off.

In the past, a number of sealing approaches have been used to seal the housing of the coupler to the coupler plug. One approach is to use an O-ring captured in place in the housing of the coupler shown for example in Karcher, et al., U.S. Pat. No. 4,833,951. A second approach is to use a cylindrical sealing surface that provides a radial seal, as shown for example in Gailey, U.S. Pat. No. 4,825,893. A third approach is to use a cut washer which abuts the extreme end surface of the coupler plug to provide the required seal. See, for example, the quick disconnect couplers shown on page 4 of the Amflo Coupler and Plug catalog. In the coupler shown in the Amflo catalog, the automatic shut-off valve is spring biased to seal against the opposed side of the cut washer.

At least in the United States, coupler plugs are not standardized. In fact, three types of coupler plugs are in common use, and they differ substantially in the outer diameter of the nose of the coupler plug, and in the axial position of the nose of the coupler plug with respect to the annular retaining groove of the plug. It would be advantageous to provide a quick disconnect coupler that seals reliably against all three commonly available coupler plugs.

A prior art approach to providing a quick disconnect coupler which is intended to seal all three commonly available plugs is to use a U cup seal in the coupler which slides axially along the length of the coupler as necessary to seal against any one of the three plugs. The structure of this prior art coupler is similar to the Hansen AUTO-FLO 20 coupler shown in various catalogs of the Tuthill Corporation, Hansen Coupling Division. In this arrangement, the coupling plug shifts the seal axially along the central passageway of the housing as necessary to bring the seal into sealing engagement with the nose of the plug. The illustrated design has a cylindrical, inwardly facing sealing surface, and the sliding seal is spring biased towards the retaining elements by the automatic shut-off valve.

SUMMARY OF THE INVENTION

This invention relates to an improved sealing arrangement for a quick disconnect coupler of the type having a housing which defines a central passageway, a plurality of retaining elements disposed on respective sides of the central passageway, means for holding the retaining elements radially inwardly, toward the central passageway, and means for manually overriding the holding means to allow the retaining elements to move radially outwardly.

According to a first aspect of this invention, a seal retaining member is movably mounted in the housing to move between first and second positions, wherein the first position is closer to the retaining elements than the second position. This seal retaining member has an opening aligned with the central passageway. Means are provided for biasing the seal retaining member toward the first position. An annular seal is mounted in the seal retaining member around the opening, and this annular seal defines an axial sealing surface facing towards the retaining elements and a radial sealing surface. The annular seal is configured such that it transmits sufficient forces to the seal retaining member to move the seal retaining member to the second position in response to a first, larger diameter plug bearing on the axial sealing surface. The annular seal is also configured to form a radial seal around a second, smaller diameter plug with the seal retaining member in the first position.

Because the annular seal relies on axial sealing for larger plugs and radial sealing for smaller plugs, the seal itself can be made with a minimum volume of a resilient material. The keeper is preferably shaped as described below to center each of the three commonly used coupler plugs. In this way, problems related to the tendency of an elastomeric material to take a compression set are reduced, and excellent sealing characteristics are provided.

According to a second aspect of this invention a seal retaining member is movably mounted in the housing to move between first and second positions, wherein the first position is closer to the retaining elements than the second position. This seal retaining member defines an opening aligned with the central passageway. At least one seal is mounted on the seal retaining member, which is biased toward the first position. The opening in the seal retaining member comprises at least first and second portions, wherein the first portion is closer to the retaining elements than the second portion, wherein the first portion is operative to center a first, larger diameter plug and defines an effective diameter of about 0.37 inch, and wherein the second portion is operative to center a second, smaller diameter plug and defines an effective diameter of about 0.32 inch.

Because the seal retaining member is free to slide axially, and because the opening of the seal defining member includes the first and second portions defined above, positive centering is provided for plugs of various diameters, thereby improving sealing characteristics of the coupler.

BRIEF DESCRIPTION OF THE DRAWINGS

FIG. 4b is a cross-sectional view taken along line 4b—4b of FIG. 4a.

FIG. 4c is a plan view taken along line 4c-4c of FIG. 4a.

DETAILED DESCRIPTION OF THE PRESENTLY PREFERRED EMBODIMENTS

Figure 1:
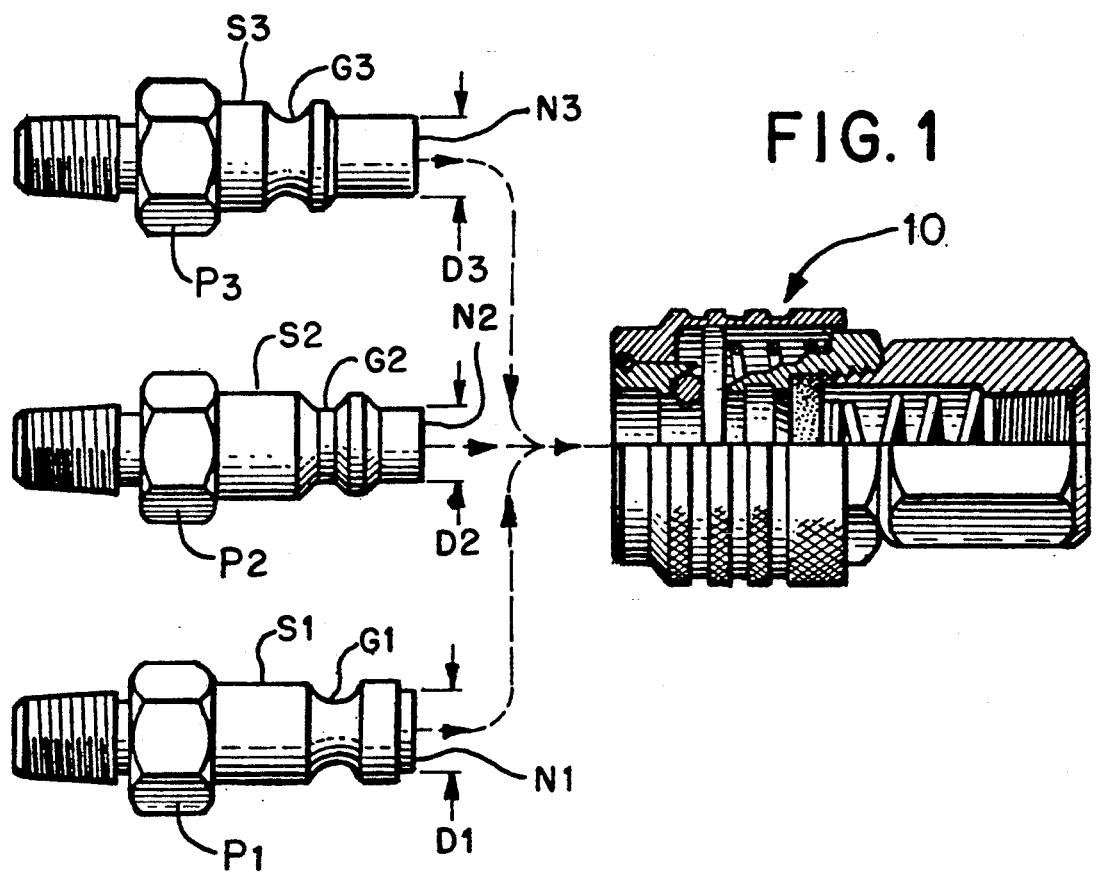
FIG. 1 is an exploded view in partial section showing a first embodiment of the coupler of this invention juxtaposed with three commonly used coupler plugs.

Turning now to the drawings, FIG. 1 shows a quick disconnect coupler 10 which incorporates a presently preferred embodiment of this invention. The coupler 10 is intended to engage and reliably seal any one of three separate coupler plugs P1, P2, P3, as shown schematically in FIG. 1.

Each of the plugs defines a shaft S1-S3 which terminates in a nose N1-N3. The shafts S1-S3 define outer diameters D1-D3. Each of the shafts S1-S3 has an intermediate groove G1-G3 that is engaged by the coupler 10 to hold the plug P1-P3 in place. The axial separation between the end of the nose N1-N3 and the groove G1-G3 varies from one plug to another, as shown in FIG. 1. Table I lists the dimensions for the diameters D1-D3 of the plugs P1-P3, which are conventional coupler plugs known as TRUFLATE short-nose type plugs, Hansen-type plugs, and ARO-type plugs respectively.

TABLE 1

| Diameter | Dimension (Inches) |
|---|---|
| D1 | 0.359-0.361 |
| D2 | 0.315-0.318 |
| D3 | 0.307-0.310 |

Figure 2:
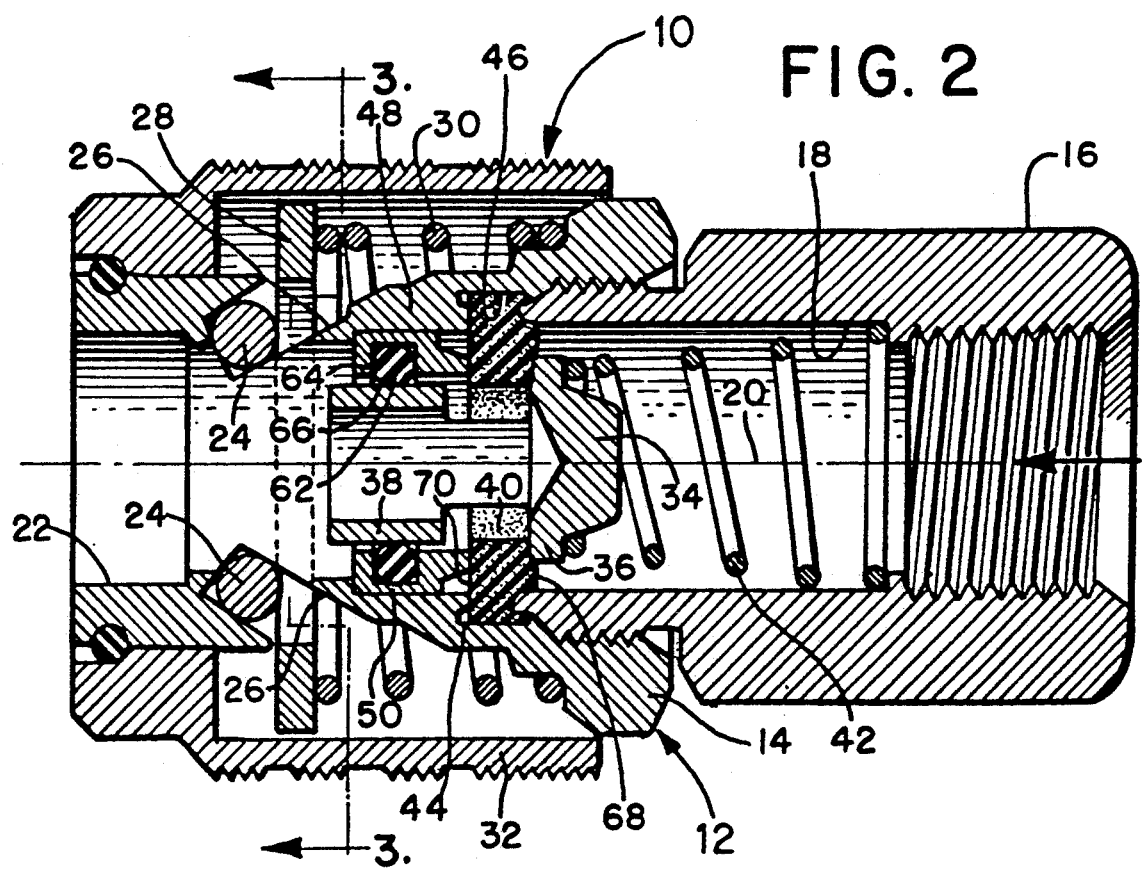
FIG. 2 is a longitudinal sectional view of the coupler of FIG. 1 showing the preferred embodiment of the seal of this invention.

FIG. 2 shows a cross-sectional view of the coupler 10, which includes a housing or housing assembly 12. The housing assembly 12 is made up of an outer housing 14 and an inner housing 16, which are threaded together to form an assembly which is rigid in use. The housing assembly 12 defines a central passageway 18 which extends along an axis 20 completely through the housing 12. The open end of the central passageway 18 at the outer housing 14 defines an entry portion 22. The entry portion 22 is sized large enough to receive the largest one of the shafts S1-S3, and in this embodiment preferably has a diameter of 0.467 inch.

Figure 3:
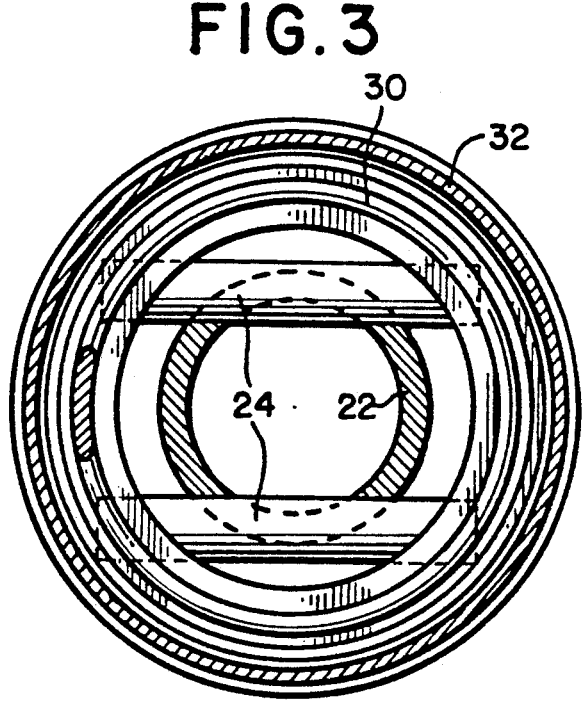
FIG. 3 is a cross-sectional view taken along line 3—3 of FIG. 2.

As shown in FIGS. 2 and 3, two retaining elements 24 are mounted in obliquely oriented slots 26 defined in the outer housing 14. The retaining elements 24 are biased radially inwardly by a washer 28 and a coil spring 30 interposed between the washer 28 and the outer housing 14. An outer sleeve 32 surrounds the washer 28 and the coil spring 30 and can be moved manually to the right as shown in FIG. 2 to compress the coil spring 30 and allow the retaining elements 24 to move radially outwardly along the slots 26, to allow one of the plugs P1-P3 to be removed from the coupler 10.

In this embodiment, the slots 26, the washer 28 and the coil spring 30 cooperate to form a biasing means that biases the retaining elements 24 radially inwardly into a plug retaining position. The outer sleeve 32 cooperates with the washer 28 to form a manual overriding means for manually overriding the coil spring 30 and allowing the retaining elements 24 to move radially outwardly.

Those skilled in the art will recognize that the retaining elements, biasing means and overriding means can take a number of alternate forms. For example, spheres or balls can be substituted for the pins 24, as shown in the Gailey and Karcher, et al. patents identified above. Similarly, the holding means can take the form of an annular sleeve, also as shown in the Gailey and Karcher, et al. patents.

As shown in FIG. 2, the coupler 10 also includes a valve member 34 mounted for axial movement in the central passageway 18. The valve member 34 defines an annular flange 36 and a tubular forward end 38. The tubular forward end 38 is pierced by a pair of slots 40, and a spring 42 is interposed between the inner housing 16 and the valve member 34 to bias the valve member 34 to the left as shown in FIG. 2. In the absence of a plug in the coupler 10, the valve member 34 is pushed against a washer 44 such that the flange 36 cooperates with the washer 44 to seal the central passageway 18. When any of the plugs P1-P3 is locked in position in the coupler 10, the nose N1-N3 of the plug P1-P3 pushes the valve member 34 to the right as shown in FIG. 2, thereby lifting the flange 36 off of the washer 44 and allowing fluid communication through the slots 40 from one end of the central passageway 18 to the other.

The outer housing 14 defines an annular groove 46 sized to receive the washer 44. This groove 46 functions as a mounting feature which is fixed in place in the housing 12 and is used to capture the washer 44 in a fixed axial position in the housing 12.

Figure 4A:
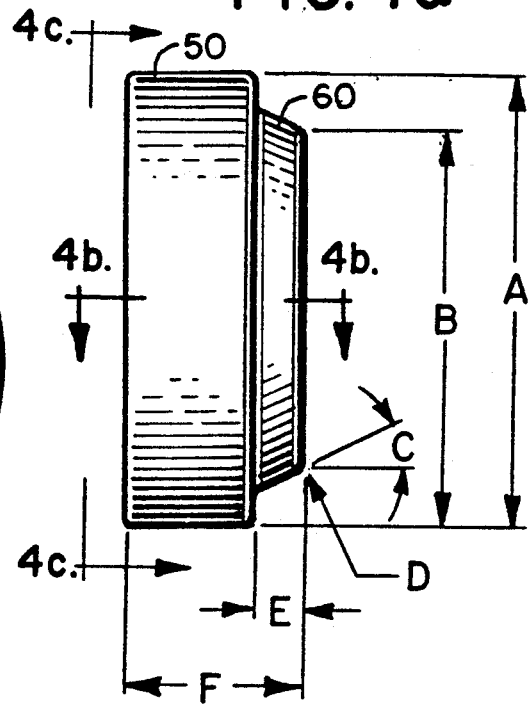
FIG. 4a is a side elevational view of the seal retainer of FIG. 2.
Figure 4C:
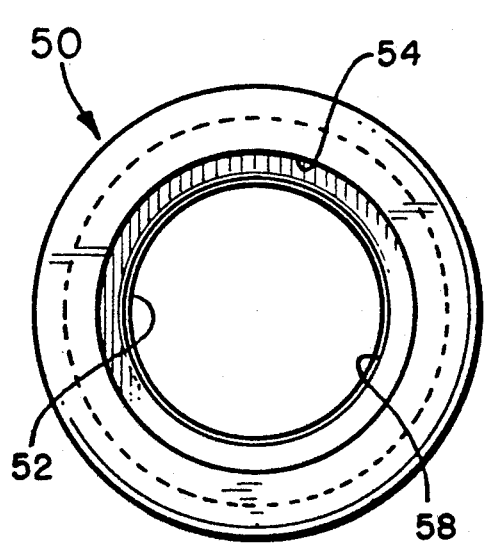

A seal retainer 50 is mounted for limited axial movement in a recess 48 formed in the housing 12 as described below in conjunction with FIGS. 5a through 5c. The seal retainer 50 is shown in greater detail in FIGS. 4a-4c.

Figure 4B:
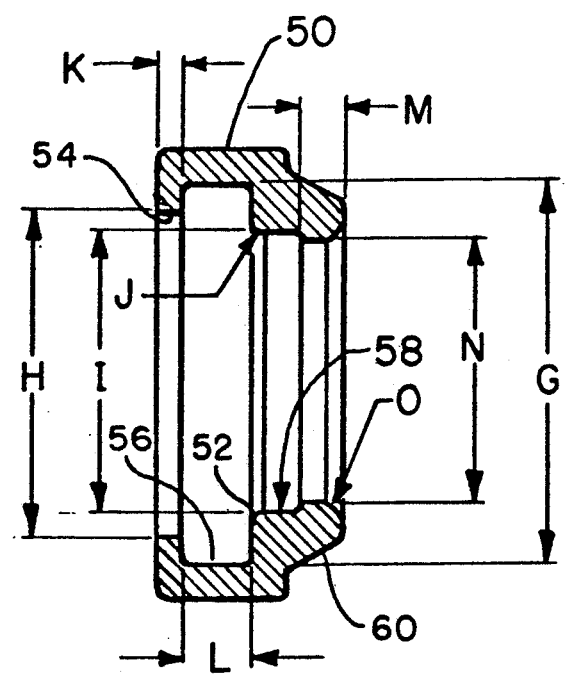

As best seen in FIG. 4b, the seal retainer 50 defines an opening 52 extending therethrough. This opening 52 includes a first portion 54 having a larger diameter, a groove 56, and a second portion 58 having a smaller diameter. The second portion 58 is in turn made up of two diameters, one slightly smaller than the other. The face of the seal retainer 50 opposite the first portion 54 defines a raised annular boss 60.

Table II provides presently preferred dimensions for the seal retainer 50, which can be made from any suitably rigid material, such as CDA 360 brass.

TABLE II

| Reference Symbol (FIGS. 4a, 4b) | Dimensions (Inches) or Angle |
|---|---|
| A | .508 |
| B | .395 |
| C | .150 |
| D | .015 R |
| E | .052 |
| F | .202 |
| G | .432 |
| H | .367 |
| I | .321 |
| J | .015 R |
| K | .027 |
| L | .083 |
| M | .040 |
| N | .313 |
| O | .015 R |

Preferably the recess 48 is dimensioned to allow about 0.07 inch of axial movement to the seal retainer 50.

In use an O-ring 62 is mounted in the groove 56. This O-ring is preferably a polyurethane ring having an inner diameter of 0.301 inch and a thickness of 0.070 inch. The preferred hardness for the O-ring 62 is 90 durometer (Shore A). A suitable O-ring may be obtained from Disogrin as Part. No. 011-90-250. As described below in conjunction with FIGS. 5a through 5c, the O-ring 62 as used with the seal retainer 50 defines an axial sealing surface 64 and a radial surface sealing 66.

Figure 5A:
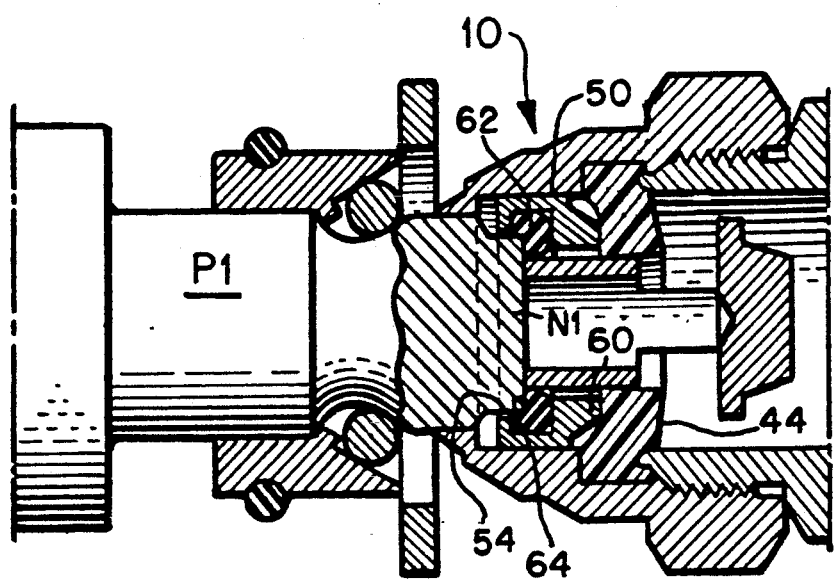
FIGS. 5a, 5b and 5c are partially schematic views of the coupler of FIGS. 1 and 2, showing the coupler mated with the plugs P1, P2, P3, respectively.
Figure 5B:
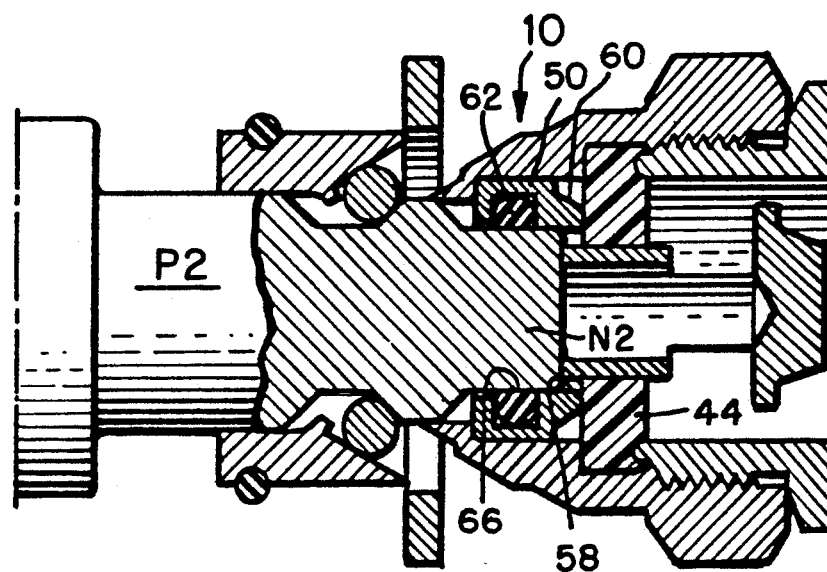
Figure 5C:
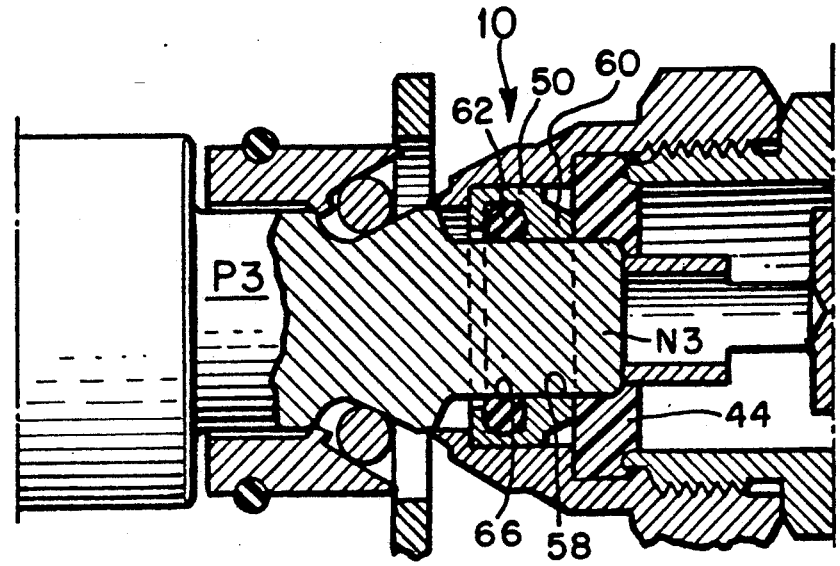

Turning now to FIGS. 5a through 5c, these drawings show in somewhat schematic form the manner in which the coupler 10 seals against the three plugs P1-P3, respectively. The plug P1 shown in FIG. 5a is the largest diameter of the three, and the nose N1 is sized to fit within the first portion 54 and to bear directly on the axial sealing surface 64 of the O-ring 62. The O-ring 62 transmits axial forces to the seal retainer 50, thereby moving the seal retainer 50 rearwardly, toward the washer 44. The boss 60 deforms the washer 44 rearwardly as shown in FIG. 5a. An axial seal is obtained between the nose N1 and the axial sealing surface 64, and between the boss 60 and the washer 44. Because the nose N1 fits within the first portion 54, the nose N1 is centered by the rigid seal retainer 50, and is held in alignment for axial sealing with the axial sealing surface 64.

As shown in FIG. 5b, the nose N2 of the plug P2 is smaller in diameter, and is sufficiently small to fit within the outer part of the second portion 58 of the seal retainer 50. Because the nose N2 is dimensioned to pass through the O-ring 62 into the outer part of the second portion 58, the seal retainer 50 is not moved rearwardly by the plug P2, and a radial seal is formed between the radial sealing surface 66 of the O-ring 62 and the nose N2. As before, an axial seal is formed between the boss 60 and the washer 44, but with less rearward deformation of the washer 44. Because the nose N2 fits within the outer part of the second portion 58, the nose N2 is held in a centered position within the central passageway 18 by the seal retainer 50. This minimizes movement of the plug P2, and facilitates adequate sealing, even when large forces are applied tending to tilt the plug P2 in the coupler 10.

FIG. 5c shows the manner in which the plug P3 is sealed by the coupler 10. Note that the nose N3 is received within the inner part of the second portion 58, and the seal retainer 50 thereby centers the plug P3. As in FIG. 5b, the plug P3 passes through the O-ring 62 and seals against the radial sealing surface 66. As before, the boss 60 forms an axial seal with the washer 44.

From the foregoing discussion of FIGS. 5a through 5c, it should be apparent that the seal retainer 50 and the O-ring 62 cooperate with the washer 44 to accommodate all three plugs P1-P3 effectively. All three of the noses N1-N3 are effectively centered by the seal retainer 50, in spite of the fact that they differ significantly in diameter and length. The O-ring 62 is dimensioned so that it is too small in diameter to provide a radial seal with the nose N1. However, the O-ring 62 is provided with a configuration and a hardness that allow the O-ring 62 to seal axially against the nose N1.

It is also significant that the washer 44 simultaneously performs four functions. First, the washer 44 defines a rearward axial face 68 that provides a sealing surface against the flange 38 of the valve number 34. Second, the washer 44 defines a forwardly facing axial face 70 that provides an axial seal against the boss 60. Third, the resilience of the washer 44 biases the seal retainer 50 to the position of FIGS. 5b and 5c, while allowing the seal retainer 50 to move rearwardly as shown in FIG. 5a. Fourth, the washer 44 seals the threaded connection between the inner and outer housings 16, 14.

Of course, it should be understood that a range of changes and modifications can be made to the preferred embodiment described above. Cut or molded parts can be used for the washer 44, and a variety of materials can be used for the respective components. It is therefore intended that the foregoing detailed description be regarded as illustrative rather than limiting, and that it be understood that it is the following claims, including all equivalents, which are intended to define the scope of this invention.

I claim:

1. In a quick disconnect coupler of the type comprising:
   a housing which defines a central passageway which extends along an axis;
   a plurality of retaining elements disposed on respective sides of the central passageway;
   means for holding the retaining elements radially inwardly, toward the central passageway;
   means for manually overriding the holding means to allow the retaining elements to move radially outwardly;
   the improvement comprising:
   a seal retaining member movably mounted in the housing to move along the axis between first and second positions, wherein the first position is closer to the retaining elements than the second position, said seal retaining member having an opening aligned with the central passageway;
   means for biasing the seal retaining member toward the first position;
   an annular seal mounted in the seal retaining member around the opening, said annular seal defining an axial sealing surface facing toward the retaining elements and a radial sealing surface;
   said annular seal being configured such that the annular seal transmits sufficient forces to the seal retaining member to move the seal retaining member to the second position in response to a first, larger diameter plug bearing on the axial sealing surface; and
   said annular seal being configured to form a radial seal around a second, smaller diameter plug with the seal retaining member in the first position.

2. The invention of claim 1 wherein the seal retaining member opening comprises a first portion oriented toward the retaining elements and a second portion oriented away from the retaining elements, wherein the first portion defines a first diameter, wherein the second portion defines a second diameter, and wherein the first diameter is greater than the second diameter.

3. The invention of claim 2 wherein the first diameter is sized to receive the first plug and wherein the second diameter is sized to receive the second plug.

4. The invention of claim 2 wherein the first diameter is about 0.37 inches and the second diameter is about 0.32 inches.

5. The invention of claim 2 wherein the seal retaining member defines a seal receiving groove between the first and second portions of the seal retaining member opening, said groove having a diameter greater than the first diameter.

6. The invention of claim 2 wherein the second portion additionally defines a third diameter, smaller than the second diameter, wherein the seal is positioned between the first and second diameters, and wherein the third diameter is farther from the seal than the second diameter.

7. The invention of claim 6 wherein the first, second and third diameters are about 0.037, 0.32 and 0.31 inches, respectively.

8. The invention of claim 1 wherein the biasing means comprises an elastomeric washer mounted in the housing adjacent the seal retaining member.

9. The invention of claim 8 wherein the seal retaining member comprises a raised annular boss positioned around the opening to contact the washer.

10. The invention of claim 8 wherein the washer defines first and second opposed faces, wherein the seal retaining member axially seals against the first face of the washer, and wherein the coupler comprises a check valve positioned in the central passageway to seal against the second face of the washer.

11. In a quick disconnect coupler of the type comprising:

a housing which defines a central passageway which extends along an axis;

a plurality of retaining elements disposed on respective sides of the central passageway;

means for holding the retaining elements radially inwardly, toward the central passageway;

means for manually overriding the holding means to allow the retaining elements to move radially outwardly;

the improvement comprising:

a seal retaining member movably mounted in the housing to move along the axis between first and second positions, wherein the first position is closer to the retaining elements than the second position, said seal retaining member having an opening aligned with the central passageway;

means for biasing the seal retaining member toward the first position;

at least one seal mounted on the seal retaining member;

said opening comprising at least first and second portions, wherein said first portion is closer to the retaining elements than the second portion, wherein said first portion is operative to center a first, larger diameter plug and defines an effective diameter of about 0.37 inch, and wherein said second portion is operative to center a second, smaller diameter plug and defines an effective diameter of about 0.32 inch.

12. The invention of claim 11 wherein said opening additionally defines a third portion, wherein said second portion is closer to the retaining elements than the third portion, and wherein said third portion is operative to center a third plug, smaller in diameter than the second plug, and defines an effective diameter of about 0.31 inch.

13. The invention of claim 11 wherein the seal retaining member defines a seal receiving groove between the first and second portions of the seal retaining member opening, said groove having a diameter greater than the first diameter.

14. The invention of claim 13 wherein the seal comprises an O-ring seal disposed in the seal receiving groove.

15. The invention of claim 11 wherein the biasing means comprises an elastomeric washer mounted in the housing adjacent the seal retaining member.

16. The invention of claim 15 wherein the seal retaining member comprises a raised annular boss positioned around the opening to contact the washer.

* * * * *